US008354561B2

(12) United States Patent
Windhorst et al.

(10) Patent No.: US 8,354,561 B2
(45) Date of Patent: Jan. 15, 2013

(54) TRIMETHYLOLPROPANE COLOR IMPROVEMENT

(75) Inventors: Kenneth A. Windhorst, Portland, TX (US); David P. Harris, Robstown, TX (US); Marcos L. Schroeder, Fort Dodge, IA (US); Fred Gaytan, Kingsville, TX (US)

(73) Assignee: Oxea Bishop LLC, Dallas, TX (US)

( * ) Notice: Subject to any disclaimer, the term of this patent is extended or adjusted under 35 U.S.C. 154(b) by 195 days.

(21) Appl. No.: 12/928,909

(22) Filed: Dec. 22, 2010

(65) Prior Publication Data

US 2011/0160494 A1    Jun. 30, 2011

Related U.S. Application Data

(60) Provisional application No. 61/284,793, filed on Dec. 24, 2009.

(51) Int. Cl.
*C07C 31/22* (2006.01)
*C07C 29/74* (2006.01)

(52) U.S. Cl. ........................................ 568/853; 568/854
(58) Field of Classification Search .................. 568/853, 568/854
See application file for complete search history.

(56) References Cited

U.S. PATENT DOCUMENTS

| 3,097,245 | A | 7/1963 | Russell et al. | 260/635 |
|---|---|---|---|---|
| 3,956,406 | A | 5/1976 | Palmer et al. | 260/637 |
| 4,514,578 | A | 4/1985 | Immel et al. | 568/853 |
| 5,603,835 | A | 2/1997 | Cheung et al. | 210/639 |
| 5,948,943 | A | 9/1999 | Supplee et al. | 568/854 |
| 6,034,284 | A | 3/2000 | Doi et al. | 568/853 |
| 6,034,285 | A | 3/2000 | Doi et al. | 568/853 |
| 6,117,277 | A | 9/2000 | Zgorzelski et al. | 203/37 |
| 6,187,971 | B1 | 2/2001 | Kratz et al. | 568/853 |
| 6,344,592 | B1 | 2/2002 | Iwamoto et al. | 568/853 |
| 6,586,642 | B2 | 7/2003 | Dernbach et al. | 568/854 |
| 6,692,616 | B2 | 2/2004 | Dernbach et al. | 203/2 |
| 7,057,080 | B2 | 6/2006 | Dernbach et al. | 568/700 |
| 7,126,018 | B2 | 10/2006 | Poppe | 554/168 |
| 7,211,701 | B2 | 5/2007 | Müller et al. | 568/853 |
| 7,253,326 | B1 | 8/2007 | Eom et al. | 568/853 |

FOREIGN PATENT DOCUMENTS

| DE | 45 078 | 1/1966 |
|---|---|---|
| DE | 287 251 A5 | 2/1991 |
| GB | 1 290 036 | 9/1972 |
| WO | WO 2008/116826 | 10/2008 |

*Primary Examiner* — Sikarl Witherspoon
(74) *Attorney, Agent, or Firm* — James J. Mullon; Michael W. Ferrell

(57) ABSTRACT

The present invention provides a process for improving the color of trimethylolpropane which comprises the steps of a) supplying a crude, aqueous base solution of trimethylolpropane, containing color causing impurities, and having a pH of less than about 9; b) contacting said base solution with an alkaline material for a period of time sufficient to increase the pH of said base solution to greater than 11 and at a sufficient temperature to allow the color causing impurities to react with said alkaline material; c) cooling the resulting solution from step (b) for a sufficient period of time; d) contacting said base solution of step (c) with an organic acid for a sufficient period of time to lower the pH thereof to less than about 9.5; e) extracting the trimethylolpropane from said base solution of step (d) with an organic solvent; f) separating the trimethylolpropane from said organic solvent; and g) purifying said trimethylolpropane from step f) to form a trimethylolpropane having a phthalic color of less than 0.20 and an acid wash color of less than 8.

8 Claims, No Drawings

TRIMETHYLOLPROPANE COLOR IMPROVEMENT

CLAIM FOR PRIORITY

This non-provisional application claims the benefit of the filing date of U.S. Provisional Patent Application Ser. No. 61/284,793, of the same title, filed Dec. 24, 2009. The priority of U.S. Provisional Patent Application Ser. No. 61/284,793 is hereby claimed and the disclosure thereof is incorporated into this application by reference.

FIELD OF THE INVENTION

This invention relates to the production of trimethylolpropane (TMP) and more particularly to obtaining low color TMP.

BACKGROUND OF THE INVENTION

Trimethylolpropane, referred to hereinbelow as TMP, is a trihydric alcohol of great industrial significance which finds use, for example, in the field of coating resin, powder coating, foam and polyester production.

Customarily, TMP is prepared from n-butyraldehyde and formaldehyde. Base-catalyzed aldol reactions initially generate 2,2-dimethylolbutyraldehyde in the 1st reaction step from n-butyraldehyde and two equivalents of formaldehyde. 2,2-dimethylolbutyraldehyde may then be converted in the 2nd reaction step, for example, by reaction with further formaldehyde and base in a Cannizzaro reaction to TMP-containing reaction mixtures in which the formate of the base used also occurs as a further reaction product.

The reaction steps 1 and 2 may either be carried out separately or in one working step. The bases used both for the base-catalyzed reaction step 1 and also for the reaction step 2 which is stoichiometric in relation to the base quantity may optionally each independently be, for example, alkali metal or alkaline earth metal hydroxides or carbonates, or tertiary amines.

When, for example, a tertiary amine is used for the separate reaction step or the reaction steps 1 and 2 carried out in a single working step, this is known as the organic Cannizzaro process. When inorganic bases, for example alkali metal or alkaline earth metal hydroxides or carbonates, are used, this is accordingly known as an inorganic Cannizzaro process. The different physical and chemical properties of the ammonium formates or inorganic formates occurring as the further reaction products require very different work-up methods for the TMP-containing reaction mixtures.

The inorganic Cannizzaro process has the advantage that the TMP occurs in good purity and when, for example, calcium hydroxide is used as the base, the by-product is calcium formate. The resultant calcium formate may be used in various applications, for example, as an additive for animal nutrition, in the building materials industry, as an assistant in the leather industry, as an assistant in producing high-gloss papers, for treating scrubbing water and in smoke desulphurization.

The TMP-containing reaction mixtures obtainable by the Cannizzaro process generally have strong coloration caused by impurities. This coloration, which may be evaluated by a color number according to APHA (American Public Health Association) or Hazen, interferes in some uses. For this reason, the work-up customarily consists of cleaning operations, for example acid treatments, extractions and/or multistage distillations. Such multistage distillations generally require expensive, space-consuming and column arrangements which are costly and inconvenient in terms of apparatus and are accordingly quite unattractive in economic terms.

Various techniques are known for the work-up of TMP-containing reaction mixtures from inorganic Cannizzaro processes. For example, German/DE patent DD-P-45 078 describes a process for work-up in which TMP-containing reaction mixtures obtained from inorganic Cannizzaro processes are admixed with secondary cycloaliphatic alcohols which form azeotropes with water. Then water is azeotropically distilled off together with this alcohol, and the precipitated alkali metal or alkaline earth metal formates are removed by filtration. After distilling off the excess alcohol, the crude TMP obtained is distilled for further purification.

DD Patent 287 251 discloses a process for removing boiling components or "high boilers" (as commonly referred to) from TMP. Examples of high boilers include subsequent reaction products of TMP, in particular formals, which have a higher boiling point than TMP and accordingly accumulate in the distillation residue when crude TMP is vacuum-distilled. In the process described, the addition of from 0.02 to 0.05 kg of acid/kg at least partially converts many of the high boilers back to TMP. In accordance with DD Patent 287 251, this process has been found to yield an increase in purified TMP.

GB 1 290 036 also describes a process for decomposing high boilers in TMP-containing reaction mixtures which have been obtained by the inorganic Cannizzaro process. This involves adding cationic exchange resins and heating to from 50° C. to 140° C. to convert any formals present, which have a similar boiling point to TMP and tend to decompose at the boiling point of TMP, to products having other boiling points which can be easily distilled off.

U.S. Pat. No. 3,097,245 to Russell et al. describes a process for preparing TMP having an APHA color number of from 50 to 200. This color number is achieved by limiting the reaction time to less than 7 hours, acidifying the reaction mixture to a pH of less than 7 and limiting the concentrations of the starting compounds to from 5 to 20% by weight. The reaction is also followed by treatment of the solution obtained with cationic exchange resins and strongly basic quaternary ammonium anion exchangers.

Common to all the processes mentioned is that chemical treatment methods have to be carried out which worsen both the eco-balance and the economic preparability of the product or entail considerable apparatus, and accordingly financial, costs and inconvenience to generate products having an acceptable color number.

While the art is replete with various processes to purify TMP, there remains a need to provide an efficient process which makes it possible to obtain pure TMP in high yield and low color from the TMP-containing reaction mixtures prepared by the inorganic Cannizzaro process. The term "low color" herein refers to a very low APHA color number, i.e., of 50 or less, typically a Phthalic (phthalic anhydride) color less than 0.4 or 0.20, and/or an ACID WASH color less than 8 as measured by the ASTM standard procedures listed below and described hereinafter.

a) ASTM, Annual Book of ASTM Standards (1987), Section 6, Volume 6.03 (Paint) Standard D 1544-80, pages 284-286.
b) ASTM, Annual Book of ASTM Standards (1961), Section 8, Standard D 1544-58T, pages 728-30.
c) "Calibration of HunterLab Color QUEST for Gardner Color", SJM 07-97.

This invention thus relates to a process for obtaining low reacted color (interchangeably referred to herein as "low color") trimethylolpropane (TMP). As previously mentioned, trimethylolpropane is produced by the condensation and cross Cannizzaro reactions of n-butyraldehyde and formaldehyde in the presence of a strong alkaline hydroxide, such as caustic solution. Removal of the TMP from the reactor solution can be carried out by the partition of the product between the aqueous solution and an organic solvent for the TMP, e.g., ethyl acetate, isobutanol, butyl acetate, and the like. The TMP is then removed from the organic layer, as for example by distillation. Another method for the removal of the TMP from the organic layer and the further removal of caustic from the TMP is to add a second solvent, one in which the TMP is insoluble, in an amount sufficient to separate the aqueous but not sufficient to separate out the TMP, remove the water layer, and then remove the first solvent by distillation. Typically the second solvent is a non-polar solvent, e.g., xylene. The TMP/second organic solvent mixture is allowed to settle and the separated TMP is removed by decantation. This latter process is set forth in Palmer et al., U.S. Pat. No. 3,956,406. These processes generally produce a product which has an acid-wash color of about 5-10 Gardner Units (GU) or phthalic anhydride color of about 100-300 APHA. Historically, the art has obtained low reacted color TMP by extracting, leaching, or further purifying color-causing impurities generated in the reaction to produce TMP.

U.S. Pat. No. 5,603,835 to Cheung et al. discloses a process which extracts color-causing impurities generated in the reaction to produce TMP. The process comprises extracting purified final TMP with an organic solvent wherein the color bodies are soluble in, but not the TMP. This extraction is reported to result in greater than about 85% yield of TMP product having an acid-wash color of 3 or less Gardner Units. The phthalic anhydride color of the TMP product is also reported to be less than about 100 APHA. It is important to note that low color TMP is not analogous to high purity TMP. The acid wash color of TMP is determined by extracting TMP with an organic solvent, followed by washing the extract with sulfuric acid, and monitoring the reacted color, e.g., through a colorimeter, to obtain a Gardner Unit (GU) value. The purity of a TMP sample is generally increased/enhanced by (re)crystallization techniques, or the like. Recrystallization may remove salts generated by the reaction of formaldehyde and butyraldehyde, but not necessarily remove color body impurities found in the TMP product. Palmer et al. (U.S. Pat. No. '406) addressed enhanced sample purity of TMP, while Cheung et al. (U.S. Pat. No. '835) addressed enhanced color of TMP. Both U.S. Pat. No. '406 and U.S. Pat. No. '835 involve a type of extraction process for the TMP product desired.

According to U.S. Pat. No. 5,948,943 to Supplee et al., crude TMP is heated in a mixture of an organic solvent and water forming a heated one phase solution, which solution is allowed to cool and to separate into at least two phases. TMP recovered from the aqueous solution exhibits an improved color. WO 2008/116826 discloses a process for the production of TMP with a low color number by treatment with activated carbon.

U.S. Pat. No. 6,117,277 to Zgorzelski et al. discloses a general process for purifying alcohols via distillation of said alcohols in the presence of small quantities of alkali metal hydroxides.

U.S. Pat. No. 7,126,018 to Poppe discloses a process for the production of polyol esters. The process consists of an esterification of a polyol, such as propylene glycol, and a fatty acid ester, such as a vegetable oil fatty acid methyl ester, in the presence of a catalyst and borohydride to yield a polyol ester having an improved color.

Further, U.S. Pat. No. 6,586,642 to Dernbach et al. teaches a hydrogenation of TMP, which has already been purified by distillation, for improving the color index.

Other prior art references relating to TMP production and color issues are U.S. Pat. Nos. 3,097,245; 3,185,274; 4,514,578; 6,034,285; 6,034,284; 6,187,971; 6,344,592; 6,692,616; 7,057,080; 7,211,701; and 7,253,326. All these references and any cited references cited herein are to be considered as incorporated herein by reference in toto.

Other processes have produced a product having various acid wash colors. However, for many applications, it is desirable to obtain a TMP product having lower acid wash colors, or other color analyses, as compared to the starting crude TMP and this low color obtained in an economically efficient manner. Thus, the art is continuously searching for methods to obtain low color TMP with increased efficiencies.

SUMMARY OF THE INVENTION

The present invention provides a process for improving the color of trimethylolpropane which comprises the steps of:
(a) supplying a crude, aqueous base solution of trimethylolpropane, containing color causing impurities, and having a pH of less than about 9;
(b) contacting said base solution with an alkaline material for a period of time sufficient to increase the pH of said base solution to greater than 11 and at a sufficient temperature to allow the color causing impurities to react with said alkaline material;
(c) cooling the resulting solution from step (b) for a sufficient period of time;
(d) contacting said base solution of step (c) with an organic acid for a sufficient period of time to lower the pH thereof to less than about 9;
(e) extracting the trimethylolpropane from said base solution of step (d) with an organic solvent;
(f) separating the trimethylolpropane from said organic solvent; and
(g) purifying said trimethylolpropane from step (f) to form a trimethylolpropane having a phthalic color of less than 0.20 and an acid wash color of less than 8.

DETAILED DESCRIPTION

This invention relates to the preparation of trimethylolpropane and relates more particularly to a method of producing trimethylolpropane from butyraldehyde and formaldehyde having increased efficiencies and improved color.

It has been found that traces of aldehydes and/or aldehyde type materials present in the crude TMP containing reaction mixture have an important adverse influence on the color index of the finished TMP product and that the addition of an alkaline material/reagent to the crude already neutralized TMP solution improves the subsequent color index. The exact mechanism of the effect of the alkaline material on these trace aldehydes and/or aldehyde materials is not known, and the applicants do not want to be limited in any way by this theory. However, the amount of the alkaline substance to be added is very limited and constitutes a critical factor in the downstream process because the alkaline substance catalyzes the transesterification of TMP and ethyl acetate or other esters in the subsequent extraction step. Such transesterification has several detrimental effects. TMP acetate (or other esters) are formed, which are very difficult to separate from the TMP. In addition, valuable TMP is converted into the acetate (ester), which decreases the yield of TMP. Because TMP is produced in a large scale production process, even a small amount of TMP acetate (esters) formed in this transesterification step results in a substantial product loss, decreased efficiencies and adverse economics.

The second part of the present invention solves this high pH issue/problem by adding an acidic compound in an amount suitable to neutralize most of the newly added alkaline material (which is added to the alkaline aqueous TMP solution just prepared); Thus, the acidic compound is added to the crude TMP highly alkaline solution just before proceeding with further processing steps such as distillation, extraction and purification.

Hence, the present invention covers an improved process for the recovery of TMP from an aqueous base solution, followed by the steps of distillation, extraction and purification (e.g., forming the crude, aqueous base TMP solution, distilling off excess formaldehydes, evaporating excess water, extraction the TMP into an organic solvent phase, which is an ester compound, and separating the TMP from said organic solvent, and finally purifying the TMP), the improvement which comprises adding an alkaline substance to the neutralized aqueous solution and then, after a sufficient period of time to allow for reaction with the color causing materials, adding an acidic substance in an amount sufficient to neutralize at least 50 mole percent by weight of the added alkaline substance immediately before the extraction with said organic solvent to obtain an organic solution of TMP which is purified in a known manner.

Surprisingly, the combination of the use of the acidic substance to effect the partial neutralization of the added alkaline substance immediately before entering the extraction step conducted with an ester compound, such as ethyl acetate, substantially reduces the color index of TMP separated from the organic extraction medium (and the purified TMP). Further. The TMP acetate formation and transesterification reactions can be suppressed effectively.

While it is known in the art, that the addition of an alkaline substance to an alcohol reduces the carbonyl number and therefore the aldehyde content in said alcohol (note U.S. Pat. No. 6,117,277 to Zgorzelski et al. and which is in a different art), but said art does not disclose any further partial neutralization with an acidic compound nor any extractive work-up of the reaction process. Furthermore, said art is not directed to any problems associated with transesterification side-reaction, and fundamentally differs from the problems associated with the present invention of preparing TMP.

In conjunction with the improved processes described above, the alkaline material is any material which can raise the crude aqueous base TMP solution from about pH 6.5-7.5 to about pH 10-14, preferably to about pH 12-13.5. Such alkaline materials include, without limitation, alkali earth materials (e.g., complexes of sodium, lithium, potassium, rubidium, cesium, and francium; preferably NAOH, KOH) and alkaline earth materials (complexes of beryllium, magnesium, calcium, strontium, barium and radium).

After the alkaline material is contacted with the crude TMP solution, it is necessary that the overall mixture be stirred over a period of time from about 1 minute to about 60 minutes, preferably from about 5 minutes to about 30 minutes, in order that the aldehyde materials are sufficiently decomposed and/or rendered inactive as to not have an adverse effect on the final color of the TMP. During this step, it is also critical that the mixture be heated to and maintained at a temperature of above about 50° C., preferably in the range of about 50° C. to about 150° C. After this heated reaction step, the resultant solution is cooled to room temperature, or a range of about 15° C. to about 30° C. before proceeding to the next step.

After this alkaline material/aldehyde material reaction step, it is then critical that the pH of the resultant TMP solution be reduced for the reasons set forth above. The pH is reduced by the addition of an organic acid in sufficient quantities to lower the pH from about 10-14 to less than about 9.5, e.g., about 7-9. Examples of organic acids include, without limitation, lactic acid, acetic acid, formic acid, citric acid, and oxalic acid.

The following subject matter is presented to further illustrate the prior art and the present invention and how the prior art can easily incorporate the present invention into their processes to achieve a greatly improved and efficient process with enhanced TMP color.

As previously mentioned, it is well known in the art to produce trimethylolpropane by the reaction, in aqueous medium, of butyraldehyde, formaldehyde and a base material such as sodium hydroxide.

It will be apparent that in this reaction, a mole of sodium formate is produced for each mole of the desired trimethylolpropane. The separation of the trimethylolpropane from the sodium formate is difficult, particularly since trimethylolpropane is infinitely soluble in water and does not readily crystallize from aqueous solutions. It has been proposed that the trimethylolpropane be isolated from the aqueous reaction mixture by evaporating a very large part of the water, then adding an organic solvent for the trimethylolpropane, which causes the sodium formate to precipitate from the mixture, and thereafter filtering off the sodium formate. The solvent is then removed by evaporation from the trimethylolpropane dissolved therein. This method does not lend itself readily to commercial operation. During the evaporation of the water, the mixture becomes so concentrated that it tends to form a solid precipitate in the apparatus. Furthermore, the trimethylolpropane thus produced still contains an appreciable amount water, sodium formate, unreacted formaldehyde and undesirable color causing materials which are objectionable for certain commercial purposes.

In accordance with the present invention (which provides the unique feature of decomposing the color causing materials), the aqueous mixture comprising trimethylolpropane, excess water, unreacted formaldehyde, and sodium formate (formed after the initial reaction), is distilled in order to remove the formaldehyde and sodium formate; (these can then be recycled back to the initial reaction vessel). The remaining mixture of TMP, water, and color causing materials are further distilled to remove additional quantities of water. At this point, the resultant mixture, having a pH of about 7-9, is contacted with sufficient quantities of an alkaline material, such as potassium hydroxide, in order to raise the pH to above about 10, preferably to about 10-14. The mixture is heated to above 50° C. and maintained thereat for approximately e.g., 30 minutes; the heat and increased pH provide the means to cause the decomposition of the color causing materials and render them harmless to the desired end color quality. The heated/reaction of the alkaline/aldehyde materials takes place over a sufficient period of time, e.g., about 1 minute to about 60 minutes, to insure the reaction is substantially complete. This resultant highly alkaline aqueous mixture is then cooled and then contacted with an aqueous organic acid, such as acetic acid, formic acid, oxalic and the like to lower the overall TMP mixture pH to a range of about 7 to 9. The TMP mixture is then subjected to an extraction step wherein the TMP is extracted with an organic solvent such as ethyl acetate to provide two immiscible phases, i.e., one, a solution of trimethylopropane in aqueous ethyl acetate, and two, the other a solution of sodium formate in water. Advantageously, this treatment is carried out in continuous countercurrent fashion using a feed mixture of trimethylolpropane and sodium formate whose water content is about 30 to 60%, preferably about 40 to 45%.

In order to recover the trimethylolpropane from the aqueous ethyl acetate, the extract may be distilled to evaporate the ethyl acetate and water. The residue from this distillation is crude trimethylolpropane containing minor amounts of less volatile impurities. Substantially pure trimethylolpropane may be obtained by distillation of this crude product at subatmospheric pressure, the trimethylolpropane boiling at about 142° C. at a pressure of 3 mm. Hg absolute.

In another method of purification/recovery, the extract of trimethylolpropane in aqueous ethyl acetate may be distilled to remove all of the water as an ethyl acetate-water azeotrope, following which the remaining extract may be treated, as by cooling, to cause crystallization of the trimethylolpropane.

The mixture of trimethylolpropane and sodium formate, referred to above, is advantageously prepared by a process which comprises the steps of continuously reacting, in an aqueous medium, a mixture of butyraldehyde, an excess of formaldehyde, and sodium hydroxide, continuously removing formaldehyde by distillation of the mixture, continuously adding KOH to the residue stream under heated conditions, cooling the resultant TMP solution, continuously adding acetic acid to the cooled TMP solution to lower the resultant solution to a pH of about 7, and then subjecting the partially neutralized TMP solution to an extraction and purification process to isolate the trimethylolpropane.

In the process of the present invention, the reactants, i.e., the formaldehyde, butyraldehyde and sodium hydroxide, are advantageously mixed together in a mixing zone to form a continuous aqueous stream comprising said reactants. For ease of handling and uniformity of mixing, and in order to initiate the reaction in the most satisfactory manner, the formaldehyde and sodium hydroxide are desirably supplied to the mixing zone in the form of aqueous solutions thereof. The reactants may be supplied to the mixing zone as individual streams thereof, or the two aldehydes may be blended together before they are mixed with the sodium hydroxide in the mixing zone. Thus, the aqueous formaldehyde may be blended with the butyraldehyde continuously to produce a stream of aqueous mixed aldehydes and the aqueous solution of alkali metal hydroxide may be injected into this stream in the mixing zone. It is less desirable to mix the sodium hydroxide separately with either aldehyde in the absence of the other aldehyde, since each of the aldehydes is susceptible to undesired autocondensation in the presence of the sodium hydroxide.

For best results, the formaldehyde is supplied to the mixing zone in substantial excess over the amount theoretically necessary for reaction with the butyraldehyde. That is, for each mole of butyraldehyde there are supplied at least about 6 moles, e.g., about 6 to 10 moles, preferably about 8 to 10 moles, of formaldehyde. Due to the use of such high proportions of formaldehyde, the reaction is more complete and the yield of trimethylolpropane is increased. Also, the use of such high proportions of formaldehyde suppresses the formation of undesired heat-sensitive compounds which make it difficult to isolate the desired trimethylolpropane from the reacted mixture.

It is also advantageous to employ an amount of sodium hydroxide which is in excess over the amount theoretically necessary for the reaction. Thus, for each mole of butyraldehyde there are preferably supplied about 1.01 to 1.2 moles of sodium hydroxide. However, too large an excess, e.g., more than about 1.5 moles of sodium hydroxide, is less desirable since it promotes side reactions and hinders the isolation of trimethylolpropane from the reaction products. On mixing, the reactants begin to react vigorously. The conditions in the mixing zone should be such that substantially complete mixing, to produce a homogeneous mixture, takes place rapidly, e.g., within a period of less than one minute. To this end, the mixing zone may be in the form of a suitably designed mixing pump, or a pipe in which there is turbulent flow, or an orifice mixer, or a vessel equipped with suitable agitator. After the mixing zone step, the reacting mixture is passed in a continuous stream through another zone where the reaction proceeds. This other zone may comprise an apparatus, i.e., a reactor, of any suitable construction; for example, a cylindrical vessel provided with internal baffles to minimize recirculation, or back-mixing, of the mixture passing through it. The capacity of the reactor and the rate of flow of the mixture therethrough are such that the material remains in the reactor for a sufficient period of time to allow the substantial completion of the reactions resulting in the formation of trimethylolpropane at the temperature of reaction.

The exothermic reaction between the butyraldehyde, formaldehyde and sodium hydroxide causes the temperature of the reaction mixture to rise. For optimum results, this temperature should rise to a peak which is within the range of about 50 to 60° C.; higher temperatures tend to cause side reactions and additional color formation, while at lower temperatures the desired reaction proceeds too slow a rate for efficient practical operation. Advantageously, the reactor is operated adiabatically, i.e., substantially without adding heat or abstracting any of the heat of reaction. Because of the presence of substantial amounts of water in the reaction mixture, the heat capacity of the mixture is relatively high so that the exothermic heat of reaction does not raise the temperature of the mixture to a level above the desired range. For example, the reactants may be mixed at an initial temperature of about 25 to 30° C. and, depending on the amount of water present, the adiabatic increase in temperature may be 25 to 30° C. The amount of water, expressed as ratio of water to butyraldehyde, is advantageously between about 15 and 16 to 1. Based on the total weight of the reaction mixture, the water content is preferably about 75 to 80%. This water content is advantageously attained, as described above, by supplying the formaldehyde and sodium hydroxide in the form of aqueous solutions therefor, the formaldehyde preferably being supplied as an aqueous solution containing about 20% of formaldehyde, by weight. When appropriate, the reactor may be heated or cooled to maintain the temperature of the reacting mixture within the optimum range, though such a procedure is less desirable than adiabatic operation.

When the mixture/solution leaves the reactor it is alkaline, generally having a pH of about 7-8, and is then subject to distillation of the crude TMP solution, in order to remove excess formaldehydes. Excess water is subsequently removed by evaporation. At this point, the pH of the resultant crude TMP solution is increased to above pH 10 and heated to at least above 50° C. in order to react with the color causing materials via aldol condensation, cross-Cannizzaro, Claisen-Schmidt Condensation, etc and decompose them and/or render them non-effective as to the color quality. This step takes place over a period of from 1 minute to about 60 minutes. The solution is then cooled and then the organic acid is added to reduce the pH to about 7-9. If this acidification is not carried out, then the high pH levels have an adverse effect on the downstream purification process.

After the addition of the acidic material if. there is any further excess unreacted formaldehyde, this can be removed by a second distillation step conducted at atmospheric or superatmospheric pressure. The formaldehyde distills over as a relatively dilute aqueous solution thereof, and sufficient water should be present in, or added to the mixture being distilled in order to insure the removal of substantially all of the unreacted formaldehyde. The aqueous distillate may be recycled, as such or after purification, to react with fresh butyraldehyde.

After the removal of the formaldehyde, the crude TMP/ reaction mixture is concentrated, by evaporation of water, to a water content of about 30 to 60%, preferably 40 to 45%, corresponding to a solids content of about 70 to 40%, preferably 60 to 55%, by weight. The resulting solution is then extracted with ethyl acetate to form two phases as described above. In one convenient and efficient extraction process, the extraction is carried out in a packed tower substantially filled with liquid. Ethyl acetate is introduced near the bottom of the tower and the aqueous solution to be treated is fed into the tower at a point above the point of introduction of the ethyl acetate. The ethyl acetate phase, which contains the trimethylolpropane as well as a minor amount of water, is less dense and is accordingly withdrawn from the top, while the other phase leaves from the bottom of the tower. It is found that the extraction proceeds most efficiently at a temperature of about 40 to 90° C., preferably about 50 to 70° C.

In one procedure, the ethyl acetate is introduced into the tower at such a rate that it forms the continuous phase therein at the point of entry of the solution to be extracted and, in fact, throughout most of the tower. In order to insure the substantially complete removal of sodium formate from the ethyl acetate phase, a stream of water is introduced into the tower at a point above the point of entry of the mixture to be extracted. Outstanding results have been obtained in this extraction when the rates of feed to the tower are such that for each pound of aqueous solution to be treated, there are supplied about 3.5 (e.g., 3.4 to 3.6) pounds of ethyl acetate and 0.15 to 0.20 pound of additional water.

In another procedure, highly effective to produce a trimethylolpropane having an extremely low potassium formate content, the ethyl acetate constitutes the discontinuous phase at the point of entry of the mixture to be extracted and, in fact, through most of the tower. The solution of trimethylolpropane in ethyl acetate obtained by the extraction procedure described above may be treated in a number of ways to recover the trimethylolpropane therefrom. In one convenient process, the ethyl acetate is removed from this solution by steam distillation, using, for example, saturated steam at atmospheric pressure, and the resulting mixture containing trimethylolpropane is vacuum flashed (e.g., at a pressure of 5 mm. Hg absolute, a liquid temperature of 180° C. and a vapor temperature of 153° C.) to remove high boilers as a residue, and the distillate from the vacuum flashing is fed into a distillation column at a point near the top of said column, said column being maintained under a subatmospheric pressure, e.g., a base pressure of 30 mm. Hg absolute. The trimethylolpropane is removed as a side stream near the base of this last column and the residue from the column is recycled to the vacuum flasher, while volatile impurities are taken off overhead.

Other methods of recovery of the trimethylolpropane include crystallization and recrystallization, as from solution of the trimethylolpropane in dry ethyl acetate. Thus, crystallization may be carried out, for example, by cooling a heated 40% solution of trimethylolpropane in ethyl acetate to a temperature of 20° C. It is often desirable, when trimethylolpropane is subjected to distillation or other operation at elevated temperature, to avoid contact between the heated trimethylollpropane and air. This helps to prevent formation of impurities. Air may be excluded, if desired, by blanketing the system with an inert gas such as nitrogen or carbon dioxide.

The following examples and analytical procedures are given to further illustrate this invention. All proportions are by weight unless otherwise indicated.

EXAMPLES

General

Acid Wash Color of Trimethylopropane (TMP)
1. Scope
    This method is used for determining the Acid Wash Color of trimethylolpropane (TMP). Results are reported in Gardner color units.
2. Applicable Documents
    1. Sartomer Company; Standard Test Method #183, revision 1; May 1990.
3. Summary of Method
    A mixture of TMP and toluene are heated to 60° C., with stirring. The toluene layer is then decanted, and mixed with a small volume of sulfuric acid. The sulfuric acid is then separated from the toluene, and the "Acid Wash Color" of the TMP is determined by measuring the Gardner color of the sulfuric acid.
4. Apparatus
    1. Hach DR/4000 spectrophotometer, or equivalent.
    2. Glass spectrophotometer sample cells, matched set, 1 cm path.
    3. Hot-plate/magnetic stirrer, or equivalent device capable of heating the sample to 62±2° C. while stirring.
    4. Glass beaker, ~150-250 ml.
    5. Analytical balance, capable of measuring ±0.1 g or better.
    6. Graduated cylinder, 50 ml.
    7. Timer.
    8. Separatory funnel, ~125 ml, with support rack.
    9. 25 ml graduated cylinder, or similar device for measuring sulfuric acid.
5. Reagents
    1. Toluene, A.C.S. reagent grade or better, having an acid wash color 1 Gardner unit.
    2. Sulfuric acid, A.C.S. reagent grade or better.
6. Safety
    1. Caution should be used when working near the heater, since it may cause burns.
    2. Appropriate PPE should be worn at all times when working with chemicals.
    3. Concentrated sulfuric acid is highly corrosive. Toluene is flammable. Avoid breathing toluene vapors. Consult the appropriate MSDS for precautions and further instructions for handling the chemicals used in this method.
7. Procedure
    Note: This method is technique sensitive. Consistent results will not be obtained unless all volumes, temperatures, etc. are measured accurately. The final color is not stable; therefore, the specified time periods for stirring, shaking, and settling must be followed exactly.
    1. Using the balance, weigh 10.0 g TMP into the beaker.
    2. Add 46.2 ml of toluene and a magnetic stir-bar to the beaker. Heat the TMP/toluene mixture to 62±2° C. while rapidly stirring the mixture with the magnetic stirrer.
    3. Stir the sample for 5.0 minutes at 60-64° C.
        Note 1: Do not allow the temperature of the mixture to exceed 64° C.
        Note 2: Begin the 5.0 minute time period when all of the TMP has melted.

4. Shut off the stirrer, and remove the mixture from the heat source. Immediately after the TMP has settled/separated, decant 37.5 ml of toluene into a graduated cylinder.
5. Transfer the toluene from the graduated cylinder into a separatory funnel, and add 12.5 ml concentrated sulfuric acid to the separatory funnel.
6. Stopper the funnel, and shake it vigorously for 30±5 seconds. Vent the funnel as necessary to relieve pressure.
7. Allow the toluene/sulfuric acid mixture to settle for 4.0 minutes. Drain enough sulfuric acid from the separatory funnel into a 1 cm UV cell to adequately fill the tube for making a Gardner color measurement.
   Note 1: Inadequate shaking in step 6 will result in low acid wash color results. If a toluene/sulfuric-acid emulsion forms that does not break apart within the 4.0 minute time period specified in step 7, repeat the analysis and shake the sample less vigorously during step 6.
8. Make sure the outer surface of the UV cell is clean and dry.
9. Measure the Gardner color of the sulfuric acid immediately after filling the UV cell. For a Hach DR/4000, the procedure is:
   a) Turn the instrument on, and allow it to complete the start-up routine.
   b) Select Hach Method 1664, "Color, Gardner".
   c) With the correct cell holder in place, insert an empty
   d) After the instrument is zeroed, remove the empty cell, insert the sample cell, and press "read".

Using HunterLab Color quest instrument:
Gardner Color read from the colorimeter:
a) Click on "SENSOR" on the tool bar of the software and select "standardize".
b) On the next window, click on "UV Out" and click on "OK".
c) Place the black card in the sample compartment so that it covers the light path completely.
d) Click on "OK" on the screen asking the user to place the black card in the sample compartment.
e) Click on "OK" and remove the black card from the sample compartment and replace with the sample holder designated for the sample tubes.
f) Place the blank sample tube in the holder. This blank sample tube should contain only 0.1 N HCl.
g) Click on "OK" at the screen asking user to place the white tile in the reflectance port.
h) Click on "OK" again.
i) Place sample tube to be read in the sample holder. Make sure that materials in the sample tube will be completely viewed in the light path.
j) Click on "READ SAM".
   Note: Sample must be in the sample compartment of the colorimeter before reading the sample.
k) Type the name of the sample in the designated area of the screen and click on "OK".
l) The result will be displayed on the screen under "Gardner-10 mm".
m) Repeat steps 1-K for reading additional samples.
n) Restandardize the colorimeter for the 20 mm cell by following steps A-H, making sure that the 20 mm cell with deionized water is used for the white tile.

8. Report
Record the Acid Wash Color in the appropriate location(s), using the Gardner color value shown on the display screen of the spectrophotometer.

9. Quality
   1. A "Blank" should be analyzed whenever a new bottle of reagent (either toluene or acid) is first used. Follow the procedure outlined above, but omit step 1 of section 7. For a blank, the solution obtained in step 7 of section 7 should have a color $\leq 1$ Gardner unit. If the blank is >1, prepare a fresh blank and/or obtain better reagents.
   2. Analytical precision and accuracy have not yet been determined for this method.
   3. This method is not currently monitored by statistical process control.

Reactive Color of Polyols Using the Gardner Color Comparison Apparatus and the Colorimeter
1. Scope
   This method describes the procedure for determining the Gardner color of Neopentyl Glycol, Pentaerythritol and trimethylolpropane when reacted with phthalic anhydride for thirty minutes at 200° C.
2. Applicable Documents
   c) ASTM, Annual Book of ASTM Standards (1987), Section 6, Volume 6.03 (Paint) Standard D 1544-80, pages 284-286.
   d) ASTM, *Annual Book of ASTM Standards* (1961), Section 8, Standard D 1544-58T, pages 728-30.
   e) "Calibration of HunterLab Color QUEST for Gardner Color", SJM 07-97.
3. Summary of Method
   This method describes the procedure for measuring Gardner color by both the colorimeter and the color comparison apparatus.
4. Apparatus
   a) Gardner/Hellige Varnish color comparison apparatus with color wheel. Color wheel having Gardner units 1 through 9.
   b) Sample tubes, 13×100 mm.
   c) HunterLab Colorimeter or equivalent.
   d) Computer
      Note: Software used in this method is HunterLab Universal Software.
   e) Hewlett-Packard DeskJet 500 printer or equivalent.
   f) Heating block, capable of controlling the temperature at 200±5° C.
   g) Vibrating mixer.
   h) Timer.
   i) Sample tube holder.
5. Reagents
   Phthalic Anhydride, ACS reagent grade (99%+).
6. Safety
   a) Caution should be used when working near the heating block, since it may cause serious burns.
   b) Gloves should be worn at all times when working with chemicals.
   c) Consult the MSDS for precautions and further instructions for handling the chemicals used in this method.
7. Procedure
   a) For all samples, place sample first in the tube, followed by the phthalic anhydride which will end up on top.
   b) For TMP samples: Place approximately 1:1 ratio of sample and phthalic anhydride in a sample tube, preferably 1.2 g each. Note: For samples such as T204 residue, use excess PA, about 1.3 g to 1.0 g of sample and after getting the instrument reading, multiply reading by 1.22 to get final result.
   c) For NPG samples: Use excess PA by measuring 1.6 g of PA and 1.0 g of samples. Multiply instrument reading by 1.3. Do not use Appendix A or subtract any factor.

d) Place the sample tube in the heating block. Make sure the temperature is 200° C. plus or minus 5° C.
e) Set the timer for 30 minutes.
f) Allow the sample tube to remain in the heating block for 10 minutes. At this time, remove the sample tube from the heating block and place the sample tube on the vibrating mixer. Stir until the sample is thoroughly mixed. Ensure that a vortex is observed when mixing the sample. Also be aware of any swirls that may develop and cause an indifferent reading.
g) Place the sample tube back into the heating block for the remaining 20 minutes.
h) After the 30 minute reaction time, pull the sample tube from the heating block and allow to cool by placing the tube in a tray filled with DI water. Leave in this tray for 5 minutes. Be sure the water does not get into the sample tube. After 5 minutes read by colorimeter. Be sure tap water is cool and not warm when touching sides of beaker. May need to change out water.
i) Wipe the outside of the sample tube to remove any materials from the reaction.

Gardner Color Read from the Colorimeter:
a. Click on "SENSOR" on the tool bar of the software and select "standardize".
b. On the next window, click on "UV Out" and click on "OK".
c. Place the black card in the sample compartment so that it covers the light path completely.
d. Click on "OK" on the screen asking the user to place the black card in the sample compartment.
e. Click on "OK" and remove the black card from the sample compartment and replace with the sample holder designated for the sample tubes.
f. Place the blank sample tube in the holder. This blank sample tube should contain only 0.1 N HCl.
g. Click on "OK" at the screen asking user to place the white tile in the reflectance port.
h. Click on "OK" again.
i. Place sample tube to be read in the sample holder. Make sure that materials in the sample tube will be completely viewed in the light path.
j. Click on "READ SAM".
   Note: Sample must be in the sample compartment of the colorimeter before reading the sample.
k. Type the name of the sample in the designated area of the screen and click on "OK".
l. The result will be displayed on the screen under "Gardner-10 mm".
m. Repeat steps I-K for reading additional samples.
n. Restandardize the colorimeter for the 20 mm cell by following steps A-H, making sure that the 20 mm cell with deionized water is used for the white tile.

Reading the Gardner Colors by the Color Comparison Wheel:
a) Place an empty sample tube in the left compartment of the color comparison apparatus.
b) Place the sample tube with the reacted sample and phthalic anhydride in the right compartment of the apparatus.
c) Note: Adjust sample tube in the compartment, so that the entire sample is being viewed.
d) Look through the eyepiece against adequate lighting.
e) Rotate the color wheel to determine the color of the sample.

8. Report
When using the colorimeter, the results attained must be corrected to the true Gardner units by using a table, see Appendix A. (A copy of Appendix A is taped to the instrument). This table is a list of Gardner units that can be read from the colorimeter along with the corrected Gardner units. This table is based on a curve generated from analyzing Gardner standards that were prepared by the ASTM method D 1544-58T, see SJM 07-97 letter. The results will be reported to the nearest whole Gardner units for lot samples and one decimal place for process samples.

9. Precision
A side-by-side study was performed on 20 samples of both pentaerythritol technical grade and trimethylolpropane, using the colorimeter and the color comparison apparatus (visual). The results from the comparison for trimethylolpropane are shown in Table 1 and the result from the comparison for pentaerythritol technical grade are shown in Table 2.

TABLE 1

| Sample | Colorimeter | Visual |
| --- | --- | --- |
| 1 | <1 | 1 |
| 2 | 2 | 2 |
| 3 | 1 | 1 |
| 4 | 2 | 3 |
| 5 | 1 | 1 |
| 6 | <1 | <1 |
| 7 | <1 | <1 |
| 8 | 3 | 3 |
| 9 | 1 | <1 |
| 10 | 1 | 1 |
| 11 | 1 | 1 |
| 12 | 1 | 1 |
| 13 | <1 | 1 |
| 14 | <1 | 1 |
| 15 | <1 | 1 |
| 16 | <1 | <1 |
| 17 | 1 | 1 |
| 18 | <1 | <1 |
| 19 | 1 | 1 |
| 20 | 1 | 1 |

TABLE 2

| sample | Colorimeter | Visual |
| --- | --- | --- |
| 1 | 1 | 1 |
| 2 | 1 | 2 |
| 3 | 1 | 1 |
| 4 | 2 | 2 |
| 5 | 1 | 2 |
| 6 | 2 | 2 |
| 7 | <1 | <1 |
| 8 | 2 | 1 |
| 9 | 2 | 1 |
| 10 | 2 | 1 |
| 11 | 2 | 1 |
| 12 | 2 | 1 |
| 13 | 2 | 1 |
| 14 | 1 | 1 |
| 15 | 2 | 2 |
| 16 | 2 | 1 |
| 17 | 1 | 1 |
| 18 | 2 | 1 |
| 19 | 2 | 1 |
| 20 | 2 | 1 |

Next, a statistical study was performed using the colorimeter on a set of 15 samples of a lot of pentaerythritol technical grade and a trimethylolpropane process sample. The results for the pentaerythritol technical grade lot indicated a % RSD of 16 by the colorimeter, whereas the % RSD was 0 by the color comparison apparatus. The results for the trimethylolpropane process sample indicated a % RSD of 27 by the colorimeter, whereas the % RSD was 32 by the color comparison apparatus.

10. Quality Control
   1. This method will be monitored by a statistical control process, in which a designated trimethylolpropane lot will be analyzed along with the daily samples.
   2. Appropriate action will be taken whenever the daily results for the monitor are not statistically "in control" and/or sample results are not within the product specification limits. Method trouble-shooting should involve experienced analysts, lab chemists, or technical advisor to determine the proper cause of action.

The correspondence of Gardner Color to APHA is substantially linear as shown by the following:

| APHA COLOR | GARDNER COLOR |
|---|---|
| 0 | 0 |
| 99 | 0.7 |
| 153 | 1.0 |
| 403 | 2.3 |

EXAMPLE 1

A crude aqueous solution of TMP was prepared using the procedure set forth in the earlier part of this specification and then subjected to distillation and evaporation. The crude TMP solution at this point was analyzed for color using the procedures set forth above. The crude TMP (pH 7.5 and 35° C.) had a Phthalic Color of 1.4 (APHA 241) and an ACID WASH color of 10. The sample of crude TMP was added to a vessel and then a 50% by weight potassium hydroxide aqueous solution was added to the vessel until the pH of the mixture was a constant 13.5. The mixture was heated to 90° C. for a period of 30 minutes and cooled to room temperature (20° C.). To the resultant cooled TMP solution in said vessel, there was added a 30% by weight formic acid until the resultant TMP mixture had stabilized at a pH of 8.0. The TMP solution was then subjected to the solvent extraction and purification procedures outlined above and then the color of the end TMP product analyzed. The final TMP product had a Phthalic color of 0.1 (APHA 21) and an ACID WASH color of 6.0

EXAMPLE 2

The procedure set forth in Example 1 was repeated with the exception that sodium hydroxide was used instead of potassium hydroxide. The crude TMP solution had a pH of 7.0 and 30° C. with a Phthalic Color of 1.1 (APHA 176) and an ACID WASH color of 11. A 55% by weight solution of sodium hydroxide was added to yield a pH of 12.1 and then the mixture was heated at 50° C. for 30 minutes and then cooled to room temperature. At this point an aqueous solution of acetic acid was added to the TMP solution to lower the pH to 7.5. The final TMP product had a Phthalic Color of 0.3 (APHA 43) and an ACID WASH of 5.0.

EXAMPLE 3

The procedure set forth in Example 1 was repeated with the exception that sodium hydroxide was used instead of potassium hydroxide. The crude TMP solution had a pH of 7.6 and 32° C. with a Phthalic Color of 1.4 (APHA 224) and an ACID WASH color of 9. A 45% by weight solution of sodium hydroxide was added to yield a pH of 12.0 and then the mixture was heated at 50° C. for 30 minutes and then cooled to room temperature. At this point an aqueous solution of acetic acid was added to the TMP solution to lower the pH to 7.8. The final TMP product had a Phthalic Color of 0.5 (APHA 72) and an ACID WASH of 6.5.

EXAMPLES 4-19

Using the information set forth in Examples 1-3 above, a two day test was conducted on the commercial production of TMP which used the procedure and process outlined above in the first part of the specification. Injection pipes were provided for the introduction of the potassium hydroxide aqueous solution into the residue of the crude TMP solution coming from the evaporator and going into a flasher vessel equipped with a heating jacket. The residue TMP solution was then fed into another vessel to reduce the temperature before proceeding. The cooled TMP residue from this latter vessel was then fitted with another injection pipe to permit introduction of acetic acid to lower the pH therefrom. Sample ports were made in order to procure samples of the TMP solutions after the KOH and acetic acid were added. Off line pH analyzers were readily available to analyze the samples in order to monitor the process conditions. During this two day period, 15 samples of TMP were collected and analyzed. The initial crude TMP solutions (15) averaged an initial Phthalic Color of 1.2 (APHA 200) and an ACID WASH color of 10.3. The KOH was a 45% aqueous solution and the average pH of the mixture after the KOH addition was 12.5. The heating was conducted for an average period of 30 minutes at a temperature of 50° C. After proceeding through the extraction and purification steps, the final TMP samples were analyzed. The average Phthalic Color for the 15 samples was 0.14 (APHA 31) and the ACID WASH color was 5.8. The reduction in color significantly improves the TMP quality and provides a highly desirable commercial product. One of the unique facets of this improved process is the fact that the overall commercial process efficiency was increased by approximately 1-2%.

Thus, it can readily be seen that this improved process provides an efficient process for the production of TMP having an ACID WASH color in the range of from about 0 to about 6 and Phthalic color in the range of from about 0 to about 50 APHA units.

While the subject matter set forth above has been directed to TMP and color improvements and increased process efficiencies thereof, another aspect of the invention is that other polyhydric alcohols can also be treated in a similar manner to achieve the desired end results. Particularly applicable are any polyhydric alcohols which can be prepared by condensing formaldehyde with higher aldehydes. Practically any alkanals with an acidic hydrogen atom in the .alpha.-position to the carbonyl group are suitable higher aldehydes. Starting materials which can be used are aliphatic aldehydes having from 2 to 24 C atoms which can be linear or branched or can also contain alicyclic groups. Other suitable starting materials are araliphatic aldehydes, provided that they contain a methylene group in the alpha.-position to the carbonyl group. In general, aralkylaldehydes having from 8 to 24 C atoms, preferably from 8 to 12 C atoms, for example phenyl-acetaldehyde, are used as starting materials. Aliphatic aldehydes having from 2 to 12 C atoms are preferred, examples being 3-ethyl-, 3-n-propyl-, 3-isopropyl-, 3-n-butyl-, 3-isobutyl-, 3-sec-butyl- and 3-tert-butyl-butanal and the corresponding n-pentanals, n-hexanals and n-heptanals; 4-ethyl-, 4-n-propyl-, 4-isopropyl-, 4-n-butyl-, 4-isobutyl-, 4-sec-butyl- and 4-tert-butyl-pentanals, -n-hexanals and -n-heptanals; 5-ethyl-, 5-n-propyl-, 5-isopropyl-, 5-n-butyl-, 5-isobutyl-, 5-sec-butyl- and 5-tert-butyl-n-hexanals and -n-heptanals;

3-methylhexanal and 3-methylheptanal; 4-methylpentanal, 4-methylheptanal, 5-methylhexanal and 5-methylheptanal; 3,3,5-trimethyl-n-pentyl-, 3,3-diethylpentyl-4,4-diethylpentyl-, 3,3-dimethyl-n-butyl-, 3,3-dimethyl-n-pentyl-, 5,5-dimethylheptyl-, 3,3-dimethylheptyl-, 3,3,4-trimethylpentyl-, 3,4-dimethylheptyl-, 3,5-dimethylheptyl-, 4,4-dimethylheptyl-, 3,3-diethylhexyl-, 4,4-dimethylhexyl-, 4,5-dimethylhexyl-, 3,4-dimethylhexyl-, 3,5-dimethylhexyl-, 3,3-dimethylhexyl-, 3,4-diethylhexyl-, 3-methyl-4-ethylpentyl-, 3-methyl-4-ethylhexyl-, 3,3,4-trimethylpentyl-, 3,4,4-trimethylpentyl-, 3,3,4-trimethylhexyl-, 3,4,4-trimethylhexyl- and 3,3,4,4-tetramethylpentylaldehyde; $C_2$ to $C_{12}$ n-alkanals are particularly preferred.

Particularly preferred polyhydric alcohols within the framework of the present invention thus are trimethylolethane, trimethylolpropane, trimethylolbutane, neopentyl glycol and pentaerythritol, trimethylolpropane being very particularly preferred.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A process for improving the color of trimethylolpropane which comprises the steps of:
    a) supplying a crude, aqueous base solution of trimethylolpropane, containing color causing impurities, and having a pH of less than about 9;
    b) contacting said base solution with an alkaline material for a period of time sufficient to increase the pH of said base solution to greater than 11 and at a sufficient temperature to allow the color causing impurities to react with said alkaline material;
    c) cooling the resulting solution from step (b) for a sufficient period of time;
    d) contacting said base solution of step (c) with an organic acid for a sufficient period of time to lower the pH thereof to less than about 9.5;
    e) extracting the trimethylolpropane from said base solution of step (d) with an organic solvent;
    f) separating the trimethylolpropane from said organic solvent; and
    g) purifying said trimethylolpropane from step (f) to form a trimethylolpropane having a phthalic color of less than 0.20 and an acid wash color of less than 8.

2. The process as set forth in claim 1, wherein the alkaline material is selected from the group consisting of alkali metal hydroxides, alkaline earth hydroxides, and mixtures thereof.

3. The process as set forth in claim 2, wherein the alkaline material is potassium or sodium hydroxide.

4. The process as set forth in claim 3, wherein in step b) the temperature is from about 50° C. to about 150° C.

5. The process as set forth in claim 4, wherein in step c) the cooling temperature is from about 10° C. to about 50° C.

6. The process as set forth in claim 5, wherein in step b), the time is from about 1 minute to about 60 minutes.

7. The process as set forth in claim 6, wherein in step d) the pH is from about 7 to about 9 and the organic acid is acetic acid.

8. In a process for the improvement of the color of trimethylolpropane (TMP) including the steps of preparing a crude aqueous solution of TMP containing color causing impurities, distilling the solution evaporating excess water from the same, extracting the TMP from the solution, and purifying the extracted TMP, the improvement which comprises the steps of adding an alkaline material to the crude TMP solution after the evaporation step to react with the color causing impurities, cooling the TMP solution and then adding an organic acid thereto to partially neutralize the TMP solution and then proceeding with the extraction and purification steps to form TMP with an improved color.

* * * * *